United States Patent
Okamoto

(10) Patent No.: US 6,465,669 B1
(45) Date of Patent: Oct. 15, 2002

(54) ORGANOMETALLIC COMPOUNDS FOR USE IN METAL-ORGANIC VAPOR-PHASE EPITAXY

(75) Inventor: Koji Okamoto, Kanagawa-ken (JP)

(73) Assignee: Tanaka Kikinzoku Kogyo K.K., Tokyo (JP)

( * ) Notice: Subject to any disclaimer, the term of this patent is extended or adjusted under 35 U.S.C. 154(b) by 0 days.

(21) Appl. No.: 09/647,888

(22) PCT Filed: Mar. 14, 2000

(86) PCT No.: PCT/JP00/01546

§ 371 (c)(1),
(2), (4) Date: Oct. 6, 2000

(87) PCT Pub. No.: WO00/58245

PCT Pub. Date: Oct. 5, 2000

(30) Foreign Application Priority Data

Mar. 29, 1999 (JP) .......................................... 11-086116

(51) Int. Cl.[7] .............................................. C07F 17/02
(52) U.S. Cl. ................................... 556/136; 427/248.1
(58) Field of Search ....................... 556/136; 427/248.1

(56) References Cited

U.S. PATENT DOCUMENTS

| | | |
|---|---|---|
| 5,130,172 A | 7/1992 | The Regents of the University of California ................. 427/252 |
| 5,929,267 A | 7/1999 | Kenkyusho ................. 556/136 |

FOREIGN PATENT DOCUMENTS

| | | |
|---|---|---|
| JP | 11-35589 | 2/1999 |

OTHER PUBLICATIONS

Abel, Edward W. et al., "Dynamic NMR studies of ring rotation in substituted ferrocenes and ruthenocenes", J. Organomet. Chem., 1991, vol. 403, No. 1–2, p. 195–208.

Kamiyama, Shinichi et al., "Synthesis of [3.3] (1,1')– and [5.5] (1,1') ruthenocenophanes and their ferrocenoruthenocenophane homologs", Bull. Chem. Soc. Jpn., 1981, vol. 54, No. 7, p. 2079–2082 Scheme 1.

*Primary Examiner*—Porfirio Nazario-Gonzalez
(74) *Attorney, Agent, or Firm*—Arent Fox Kintner Plotkin & Kahn

(57) ABSTRACT

The present invention is directed to organic ruthenium compounds and organic platinum compounds which provide a constant film-forming rate and have excellent thermal stability. In the organic ruthenium compounds, at least one substituent in 5-membered rings contains an alkyl group selected from $CH_2CH_3$, $CH_2CH_2CH_3$, $CH_2CH_2CH_2CH_3$, $C(CH_3)_3$, $CH_2(C_6H_5)$, $COCH_3$, $COOCH_3$, and $CH_2OCH_3$. In the organic platinum compounds, at least one substituent in the 5-membered ring of $R_1$, $R_2$, $R_3$, $R_4$, and $R_5$ contains an alkyl group selected from $CH_3$, $CH_2CH_3$, $CH_2CH_2CH_3$, $CH_2CH_2CH_2CH_3$, $C(CH_3)_3$, and $CH_2(C_6H_5)$.

2 Claims, 1 Drawing Sheet

ORGANOMETALLIC COMPOUNDS FOR USE IN METAL-ORGANIC VAPOR-PHASE EPITAXY

TECHNICAL FIELD

The present invention relates to organometallic compounds which are used for forming thin film comprising ruthenium, ruthenium oxide, or high-purity platinum on a substrate through metal-organic vapor-phase epitaxy. More particularly, the present invention relates to such organometallic compounds which are useful for producing, for example, electrode material used in semiconductor devices and parts.

BACKGROUND ART

Conventionally, in advanced technical fields related for example to electrode materials for semiconductor devices, organic ruthenium compounds and organic platinum compounds have been employed for forming a variety of ruthenium thin films and platinum thin films through metal-organic vapor-phase epitaxy. In order to form a ruthenium thin film, ruthenocene; i.e., an organic ruthenium compound represented by formula 3:

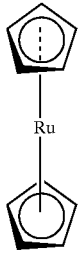

is employed as a source.

The organic ruthenium compound represented by formula 3 has 5-membered rings containing exclusively carbon atoms and hydrogen atoms. In this compound, a ruthenium atom is sandwiched by two 5-membered rings.

In order to produce a platinum thin film, a compound represented by formula 4:

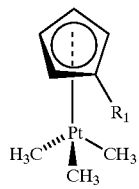

has conventionally been employed as a source compound. In this organic platinum compound, one 5-membered ring; i.e., a cyclopentadiene ring, forms a bond with the platinum atom, and three methyl groups serve as ligands or form bonds with the platinum atom.

However, the organic ruthenium compound represented by formula 3 has a melting point of 198° C. Moreover, an organic platinum compound represented by formula 4 in which $R_1$ is H has a melting point of 65° C., and a similar compound in which $R_1$ is $CH_3$ has a melting point as high as 30° C. These compounds have relatively low vapor pressure, and control of vaporization rate thereof is disadvantageously difficult.

Difficulty in controlling vaporization rate induces variation in thin-film-formation rate, and results in production of thin film lacking in accurately controlled thickness and flatness.

In addition, the aforementioned ruthenium compound and platinum compounds may be decomposed during heating for vaporization. Thus, poor thermal stability thereof is pointed out in the actual production field.

In recent years, there has been persistent demand for further size-reduction in electronic apparatus, and the target level of integration and packaging density of semiconductor devices and parts has further increased. Accordingly, ruthenium thin film, ruthenium oxide thin film, and high-purity platinum thin film which are incorporated into semiconductor devices and parts are required to have a further smaller thickness.

In connection with such a technical trend, so long as compounds exhibiting a variable film-formation rate are employed as sources, strict quality control of produced thin film cannot be attained, thereby generating variation in quality among products. This problem becomes grave as the thickness of devices decreases and the target film thickness decreases further. Unless the problem is solved, formation of thin film by using conventional source compounds inevitably faces a limitation and does not satisfy demands in the market.

DISCLOSURE OF THE INVENTION

In view of the foregoing, the present inventor has conducted earnest studies, and have developed organometallic compounds which solve the drawbacks of the conventional organic ruthenium compound represented by formula 3 and organic platinum compounds represented by formula 4.

In general, a process for forming thin film broadly comprises three steps: (1) vaporizing a source so as to permit feeding of the source onto a substrate; (2) feeding the vaporized source onto the substrate; and (3) depositing particles of the fed source on the substrate. In metal-organic vapor-phase epitaxy, a compound source is typically used instead of an elemental source.

The reason for not using an elemental source is that the source itself has a relatively low vapor pressure and is difficult to feed. Therefore, the elemental source is converted to a compound source having a relatively high vapor pressure so as to transport the source. However, when the organic ruthenium compound represented by formula 3 and organic platinum compounds represented by formula 4 are employed as sources, a constant film-formation rate is not obtained, possibly due to a low vapor pressure of the sources.

If the vapor pressure of a source is a sole issue to be considered, increasing the molecular weight of the source would be the easiest solution. However, ruthenium thin film, ruthenium oxide thin film, and high-purity platinum thin film which are employed in the semiconductor industry must have a high level of quality which cannot be attained by such a simple approach. For example, to meet the required quality and properties, several factors must be considered, which include crystalline state, lattice constant, thermal expansion coefficient, control of structural defects, mutual diffusion of impurities and constitutional elements, and selective growth.

The organic ruthenium compounds and organic platinum compounds according to the present invention exhibit sufficiently high vapor pressure during vaporization, and thin film obtained from the compounds satisfies properties and quality required in the semiconductor industry.

Accordingly, in claim 1 of the present invention, there is provided an organic ruthenium compound for forming ruthenium thin film or ruthenium oxide thin film on a substrate through metal-organic vapor-phase epitaxy, represented by structural formula 1:

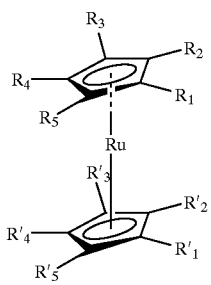

wherein at least one of the substituents $R_1$, $R_2$, $R_3$, $R_4$, $R_5$, $R_1'$, $R_2'$, $R_3'$, $R_4'$, and $R_5'$ in the two 5-membered rings comprises an alkyl group selected from $CH_2CH_3$, $CH_2CH_2CH_3$, $CH_2CH_2CH_2CH_3$, $C(CH_3)_3$, $CH_2(C_6H_5)$, $COCH_3$, $COOCH_3$, and $CH_2OCH_3$;, with the case in which $R_1$, $R_2$, $R_3$, $R_4$, $R_5$, $R_1'$, $R_2'$, $R_3'$, $R_4'$, and $R_5'$ all represent hydrogen atoms being excluded.

The above exclusion is made so as to clarify that the ruthenium compounds of the present invention do not include the conventional organic ruthenium compound represented by formula 3 and other known organic ruthenium compounds. Even though conventionally known organic ruthenium compounds are employed as sources of metal-organic vapor-phase epitaxy, vaporization rate is not as constant as that of the organic ruthenium compounds of the present invention. The ruthenium compounds of the present invention represented by structural formula 1 are more bulky than conventionally known organic ruthenium compounds and have increased thermal stability.

Thus, the organic ruthenium compounds of the present invention are characterized in that at least one of the substituents in the 5-membered cyclopentadiene ring comprises an alkyl group selected from $CH_2CH_3$, $CH_2CH_2CH_3$, $CH_2CH_2CH_2CH_3$, $C(CH_3)_3$, $CH_2(C_6H_5)$, $COCH_3$, $COOCH_3$, and $CH_2OCH_3$; with the aforementioned case being excluded.

Since in the ruthenium compounds of formula 1 of the present invention, at least one of the substituents of the cyclopentadiene ring has $CH_2CH_3$, $CH_2CH_2CH_3$, $CH_2CH_2CH_2CH_3$, $C(CH_3)_3$, $CH_2(C_6H_5)$, $COCH_3$, $COOCH_3$, and $CH_2OCH_3$, the molecular weight of the compounds is larger than that of ruthenocene represented by formula 2. As a result, vapor pressure of the vaporized compounds serving as deposition sources increases and a constant vaporization rate is attained as compared with the case of conventional ruthenocene.

In claim 2 of the present invention, there is provided an organic platinum compound for forming platinum thin film on a substrate through metal-organic vapor-phase epitaxy, represented by structural formula 2:

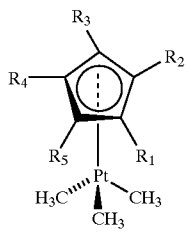

wherein at least one of the substituents $R_1$, $R_2$, $R_3$, $R_4$, and $R_5$ in 5-membered rings comprises an alkyl group selected from $CH_3$, $CH_2CH_3$, $CH_2CH_2CH_3$, $CH_2CH_2CH_2CH_3$, $C(CH_3)_3$, and $CH_2(C_6H_5)$.

In the above compounds, the case in which $R_1$, $R_2$, $R_3$, $R_4$, and $R_5$ all represent $CH_3$ groups and the case in which only $R_1$ is a $CH_3$ group are excluded. The exclusion is made so as to clarify that the platinum compounds of the present invention do not include the conventional organic platinum compounds represented by formula 4 and other known organic platinum compounds. Even though conventionally known organic platinum compounds are employed as sources of metal-organic vapor-phase epitaxy, vaporization rate is not as constant as that of the organic platinum compounds of the present invention.

In the organic platinum compound of the present invention represented by structural formula 2, at least one substituent in the 5-membered cyclopentadiene ring comprises an alkyl group selected from $CH_3$, $CH_2CH_3$, $CH_2CH_2CH_3$, $CH_2CH_2CH_2CH_3$, $C(CH_3)_3$, and $CH_2(C_6H_5)$, thereby providing more bulky molecules and elevating the molecular weight of the compounds as compared with conventional organic platinum compounds represented by formula 4. As a result, vapor pressure of the vaporized compounds is higher than conventional organic platinum compounds, bulkiness also increases, and a constant vaporization rate is attained.

Since the organometallic compounds represented by the aforementioned formulas 1 and 2 have a bulky alkyl group attached to a cyclopentadiene ring, other reactive elements encounter difficulty in approaching Ru or Pt. Therefore, decomposition to metallic platinum or platinum oxide is prevented as compared with the case of organic platinum compounds represented by formula 2. Thus, the organometallic compounds as described in claims 1 and 2 exhibit constant vaporization characteristic and thermal stability when they serve as compound sources of metal-organic vapor-phase epitaxy.

In addition, substituents selected in the present invention contain carbon and hydrogen, and optionally oxygen, depending on the substituents, and contain no other constitutional element. Thus, the amounts of impurities in the formed thin film do not increase. Particularly, a formed platinum film shows considerably high purity without losing the aforementioned characteristics so far as research has determined.

Several methods are contemplated for producing organic ruthenium compounds and organic platinum compounds. The methods will next be described by way of examples.

BEST MODES FOR CARRYING OUT THE INVENTION

Figure 1:
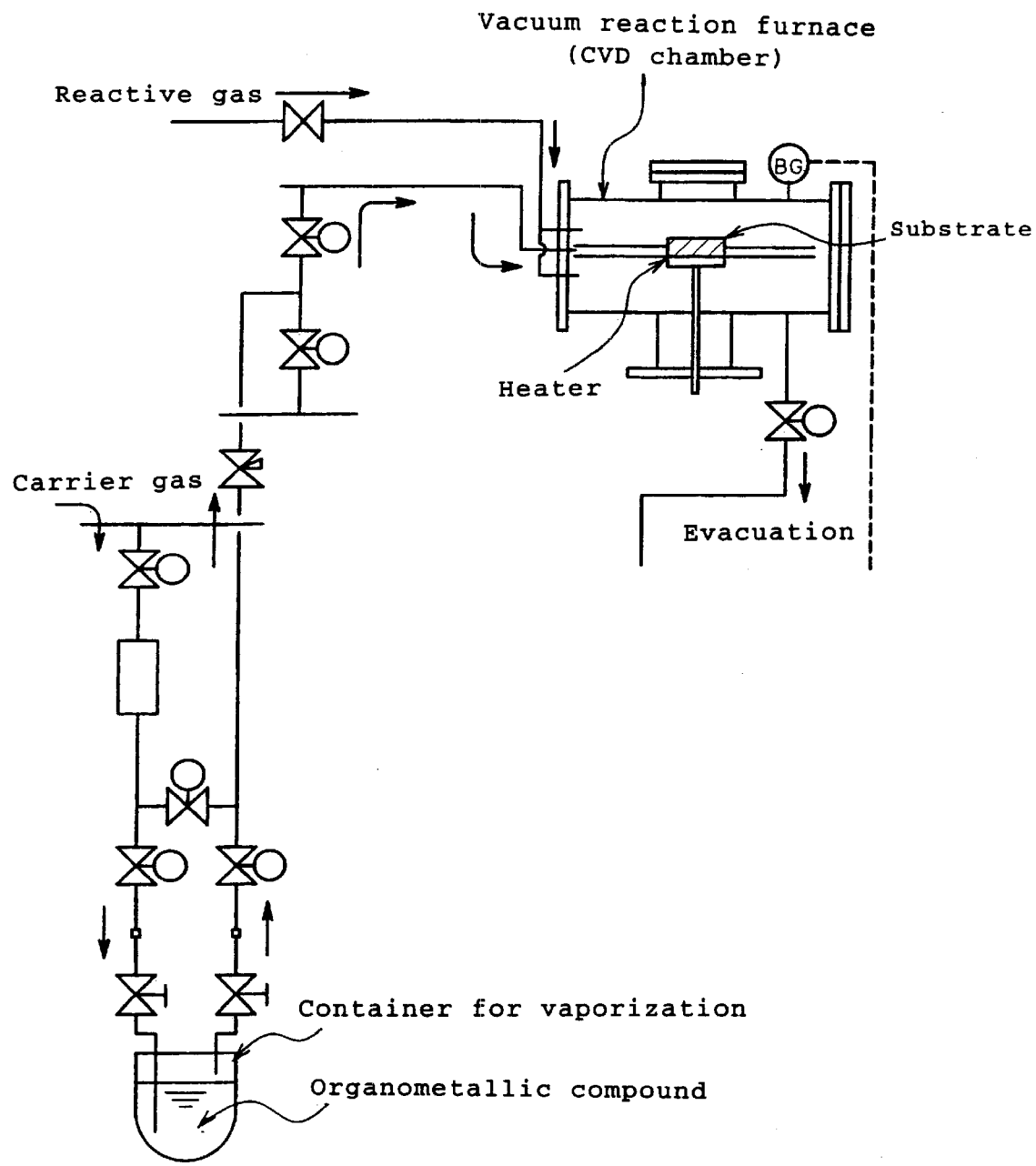
FIG. 1 is a schematic representation showing an MOCVD apparatus employed in embodiments for carrying out the present invention.

The organic ruthenium compounds and the organic platinum compounds of the present invention for employment in metal-organic vapor-phase epitaxy will next be described with reference to best modes for carrying out the invention. The organic ruthenium compounds and the organic platinum compounds are described separately.

A. ORGANIC RUTHENIUM COMPOUNDS

Embodiment 1

Ruthenium chloride (466 g) and trimethylsilylethylcyclopentadiene (1205 g) were dissolved in ethyl alcohol (22524 ml), and the mixture was refluxed for 24 hours. After reflux had been completed, the reaction mixture was subjected to extraction by using ethyl ether, and the solvent component was removed through distillation, to thereby yield 428 g of bis(ethylcyclopentadiene)ruthenium having a melting point of 130° C.

By using the thus-prepared bis(ethylcyclopentadiene) ruthenium, metal-organic vapor-phase epitaxy was carried out in an MOCVD apparatus shown in FIG. 1, to thereby form ruthenium thin film having a thickness of 1.19 $\mu$m on a glass substrate. Vaporization rate of the compound was constant at 0.03 $\mu$m/minute, and the formed film has variation in thickness of ±0.001 $\mu$m.

The following conditions for forming ruthenium thin film in the MOCVD apparatus were employed: vacuum of 0.5 Torr; substrate temperature of 200° C.; sample temperature of 50° C.; carrier gas of argon (80 ccm); and reactive gas of hydrogen (50 ccm). These conditions were also employed in the following Embodiments.

Embodiment 2

Ruthenium chloride (466 g) and (benzyl)(trimethylsilyl) cyclopentadiene (1773 g) were dissolved in ethyl alcohol (22524 ml), and the mixture was refluxed for 24 hours. After reflux had been completed, the reaction mixture was subjected to extraction by using ethyl alcohol, and the solvent component was removed through distillation, to thereby yield 857 g of bis(benzyl)(cyclopentadienyl)ruthenium having a melting point of 135° C.

By using the thus-prepared bis(benzyl)(cyclopentadienyl) ruthenium, metal-organic vapor-phase epitaxy was carried out in the MOCVD apparatus shown in FIG. 1, to thereby form ruthenium thin film having a thickness of 0.76 $\mu$m on a glass substrate. Vaporization rate of the compound was constant at 0.02 $\mu$m/minute, and the formed film has variation in thickness of ±0.013 $\mu$m.

Embodiment 3

A dichloro(η-cycloocta-1,5-diene)ruthenium (II) polymer (1190 g) and t-butylcyclopentadienylthallium (2295 g) were dissolved in 1,2-dimethoxyethane (22000 ml), and the mixture was refluxed for 2 hours. After reflux had been completed, the reaction mixture was subjected to extraction by using ethyl alcohol, and the solvent component was removed through distillation, to thereby yield 765 g of bis(t-butylcyclopentadiene)ruthenium having a melting point of 140° C.

By using the thus-prepared bis(t-butylcyclopentadiene) ruthenium, metal-organic vapor-phase epitaxy was carried out in the MOCVD apparatus shown in FIG. 1, to thereby form ruthenium thin film having a thickness of 1.28 $\mu$m on a glass substrate. Vaporization rate of the compound was constant at 0.032 $\mu$m/minute, and the formed film has variation in thickness of ±0.003 $\mu$m.

Embodiment 4

A dichloro(η-cycloocta-1,5-diene)ruthenium (II) polymer (1190 g) and propylcyclopentadienyl tributyltin (4533 g) were dissolved in 1,2-dimethoxyethane (22000 ml), and the mixture was refluxed for 48 hours. After reflux had been completed, the reaction mixture was cooled to room temperature, to thereby yield 765 g of bis(propylcyclopentadiene)ruthenium having a melting point of 135° C.

By using the thus-prepared bis(propylclopentadiene) ruthenium, metal-organic vapor-phase epitaxy was carried out in the MOCVD apparatus shown in FIG. 1, to thereby form ruthenium thin film having a thickness of 1.20 $\mu$m on a glass substrate. Vaporization rate of the compound was constant at 0.030 $\mu$m/minute, and the formed film has variation in thickness of ±0.002 $\mu$m.

Embodiment 5

Acetylferrocene (3 mol) and ruthenium chloride (1 mol) were mixed, and the mixture was allowed to react at 250° C. for two days, thereby yielding target acetylruthenocene with a yield of 50%.

By using the thus-prepared acetylruthenocene, metal-organic vapor-phase epitaxy was carried out in the MOCVD apparatus shown in FIG. 1, to thereby form ruthenium thin film having a thickness of 1.10 $\mu$m on a glass substrate. Vaporization rate of the compound was constant at 0.025 $\mu$m/minute, and the formed film has variation in thickness of ±0.002 $\mu$m.

In order to confirm the effect of organic ruthenium compounds of the present invention, the present inventor employed ruthenocene represented by formula 3 serving as comparative compound 1. By using comparative compound 1, metal-organic vapor-phase epitaxy was carried out in the apparatus shown in FIG. 1, to thereby form ruthenium thin film. Film formation by using comparative compound 1 was compared with that by using the organic ruthenium compounds of the present invention.

Comparative compound 2 was prepared as follows. Ruthenium chloride (466 g) and pentamethylcyclopentadienyltrimethylsilane (1653 g) were dissolved in ethyl alcohol (22524 ml), and the mixture was refluxed for 24 hours. After reflux had been completed, the reaction mixture was subjected to extraction by using ethyl alcohol, and the solvent component was removed through distillation, to thereby yield 482 g of $CH_3$-substituted bis(pentamethylcyclopentadienyl)ruthenium having a melting point of 250° C. serving as a comparative source.

By using bis(pentamethylcyclopentadienyl)ruthenium, metal-organic vapor-phase epitaxy was carried out in the apparatus shown in FIG. 1, to thereby form ruthenium thin film. Film formation by using the compound was compared with that by using the organic ruthenium compounds according to the aforementioned Embodiments.

Further, comparative compound 3 was prepared as follows. Ruthenium chloride (1000 g) and ethyl alcohol (3000 ml) were mixed, and the mixture was stirred at room temperature for three hours. A methylcyclopentadiene dimer was distilled to prepare methylcyclopentadiene (3500 ml).

Ruthenium chloride and ethyl alcohol were mixed, and the mixture was stirred at room temperature for three hours. The above methylcyclopentadiene and zinc powder (3000 g) were added to the mixture, and the resultant mixture was allowed to react at room temperature for four days. The reaction mixture was subjected to extraction by using benzene, and the solvent component was removed through distillation, to thereby yield 1000 g of $CH_3$-substituted bis(methylcyclopentadiene)ruthenium serving as a comparative source.

By using bis(methylcyclopentadiene)ruthenium, metal-organic vapor-phase epitaxy was carried out in an apparatus shown in FIG. 1, to thereby form ruthenium thin film. Film formation by using the compound was compared with that by using the organic ruthenium compounds according to the aforementioned Embodiments.

By using the organic ruthenium compounds obtained the aforementioned Embodiments and comparative compounds, metal-organic vapor-phase epitaxy was carried out in the MOCVD apparatus shown in FIG. 1, to thereby form the corresponding ruthenium thin films. The thickness of each film was measured as time elapsed, and comparison was carried out so as to confirm the effect of the compounds of the present invention. The results are summarized in Table 1.

TABLE 1

| Organic ruthenium compounds | Film thickness ($\mu$m) | | | | |
| --- | --- | --- | --- | --- | --- |
| | 5 min after | 10 min after | 20 min after | 30 min after | 40 min after |
| Embodiment 1 | 0.15 | 0.31 | 0.59 | 0.90 | 1.19 |
| Embodiment 2 | 0.10 | 0.22 | 0.48 | 0.63 | 0.76 |
| Embodiment 3 | 0.16 | 0.33 | 0.64 | 0.97 | 1.28 |
| Embodiment 4 | 0.15 | 0.30 | 0.60 | 0.89 | 1.20 |
| Embodiment 5 | 0.13 | 0.25 | 0.50 | 0.75 | 1.01 |
| Comp. compound 1 | 0.10 | 0.25 | 0.60 | 1.20 | 1.50 |
| Comp. compound 2 | 0.05 | 0.15 | 0.50 | 1.10 | 1.50 |
| Comp. compound 3 | 0.12 | 0.19 | 0.36 | 0.46 | 0.96 |

From the results shown in Table 1, the film-formation rate in each interval of measurement was calculated. The results are shown in Table 2.

TABLE 2

| Organic ruthenium compounds | Film-formation rate ($\mu$m/minute) | | | | |
| --- | --- | --- | --- | --- | --- |
| | 0–5 min | 5–10 min | 10–20 min | 20–30 min | 30–40 min |
| Embodiment 1 | 0.030 | 0.032 | 0.028 | 0.031 | 0.029 |
| Embodiment 2 | 0.020 | 0.024 | 0.026 | 0.015 | 0.013 |
| Embodiment 3 | 0.032 | 0.034 | 0.031 | 0.033 | 0.031 |
| Embodiment 4 | 0.030 | 0.030 | 0.030 | 0.029 | 0.031 |
| Embodiment 5 | 0.026 | 0.024 | 0.025 | 0.025 | 0.026 |
| Comp. compound 1 | 0.020 | 0.030 | 0.045 | 0.060 | 0.030 |
| Comp. compound 2 | 0.010 | 0.020 | 0.035 | 0.060 | 0.040 |
| Comp. compound 3 | 0.024 | 0.014 | 0.017 | 0.010 | 0.050 |

As is clear from the results, the organic ruthenium compounds of the present invention exhibit considerably constant vaporization rate, thereby providing constant film-formation rate as compared with conventional organic ruthenium compounds.

B. ORGANIC PLATINUM COMPOUNDS

Embodiment 6 trimethylplatinum iodide (0.28 g) and ethylcyclopentadienylsodium (0.4 M) were added into tetrahydrofuran (1.95 ml) at room temperature, and the mixture was stirred for 10 minutes. The tetrahydrofuran was removed through distillation, to thereby yield 0.075 g of trimethyl (ethylcyclopentadiene)platinum.

By using the thus-prepared trimethyl (ethylcyclopentadiene)platinum, metal-organic vapor-phase epitaxy was carried out in the MOCVD apparatus shown in FIG. 1, to thereby form high-purity platinum thin film having a thickness of 0.21 $\mu$m on an SiO$_2$ substrate. Vaporization rate of the compound was constant at 0.007 $\mu$m/minute, and the formed film has variation in thickness of ±0.002 $\mu$m.

The following conditions for forming platinum thin film in the MOCVD apparatus were employed: vacuum of 1.0 Torr; substrate temperature of 200° C.; sample temperature of 50° C.; carrier gas of argon (30 ccm); and reactive gas of hydrogen (40 ccm). These conditions were also employed in the following Embodiment.

The present inventor further formed platinum thin film by using an organic platinum compound represented by formula 4 in which R1 is H, which served as a comparative compound source. Metal-organic vapor-phase epitaxy was carried out in the MOCVD apparatus shown in FIG. 1. The thickness of each film was measured as time elapsed, and comparison was carried out so as to confirm the effect of the compound of the present invention. The results are summarized in Table 3.

TABLE 3

| Organic platinum compounds | Film thickness ($\mu$m) | | | | |
| --- | --- | --- | --- | --- | --- |
| | 2 min after | 4 min after | 8 min after | 16 min after | 30 min after |
| Embodiment 6 | 0.015 | 0.031 | 0.056 | 0.111 | 0.210 |
| Comp. compound | 0.010 | 0.016 | 0.024 | 0.112 | 0.240 |

From the results shown in Table 3, the film-formation rate in each interval of measurement was calculated. The results are shown in Table 4.

TABLE 4

| Organic platinum compounds | Film-formation rate ($\mu$m/minute) | | | | |
| --- | --- | --- | --- | --- | --- |
| | 0–2 min | 2–4 min | 4–8 min | 8–16 min | 16–30 min |
| Embodiment 6 | 0.008 | 0.008 | 0.006 | 0.007 | 0.007 |
| Comp. compound | 0.005 | 0.001 | 0.002 | 0.011 | 0.009 |

As is clear from the results, the organic platinum compounds of the present invention exhibit considerably constant vaporization rate, thereby providing constant film-formation rate as compared with conventional organic platinum compounds.

Industrial Applicability

By using the organic ruthenium compounds and organic platinum compounds of the present invention in metal-organic vapor-phase epitaxy, vaporization rate of the sources is readily controlled and thin-film-formation rate becomes constant, thereby forming ruthenium thin film and platinum thin film having an accurately controlled thickness. In addition, the organic platinum compounds of the present invention do not decompose during heating for vaporization and have excellent thermal stability. Thus, the present invention satisfies a possible demand for further size-reduction, and enhances the level of integration and packaging density of semiconductor devices and parts.

What is claimed is:

1. An organometallic compound for forming a ruthenium thin film or ruthenium oxide thin film on a substrate through metal-organic vapor-phase epitaxy, represented by the following structural formula 1:

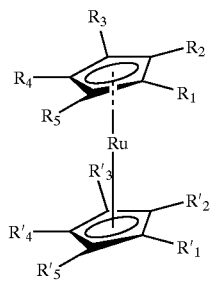

wherein only one of the substituents $R_1$, $R_2$, $R_3$, $R_4$, $R_5$, $R_1'$, $R_2'$, $R_3'$, $R_4'$ and $R_5'$ is a propyl group, with the remainder being hydrogen.

2. An organometallic compound for forming a ruthenium thin film or ruthenium oxide thin film on a substrate through metal-organic vapor-phase epitaxy, represented by the following structural formula 1:

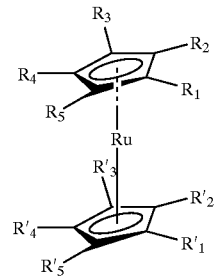

wherein only one of the substituents $R_1$, $R_2$, $R_3$, $R_4$, $R_5$, $R_1'$, $R_2'$, $R_3'$, $R_4'$ and $R_5'$ is a n-butyl group, with the remainder being hydrogen.

* * * * *